(12) United States Patent
Lorenz

(10) Patent No.: US 9,067,874 B2
(45) Date of Patent: Jun. 30, 2015

(54) METHOD FOR PRODUCING POLYETHER POLYOLS

(75) Inventor: Klaus Lorenz, Dormagen, DE (US)

(73) Assignee: Bayer Intellectual Property GmbH, Monheim (DE)

( * ) Notice: Subject to any disclaimer, the term of this patent is extended or adjusted under 35 U.S.C. 154(b) by 359 days.

(21) Appl. No.: 13/582,786

(22) PCT Filed: Mar. 9, 2011

(86) PCT No.: PCT/EP2011/053501
§ 371 (c)(1),
(2), (4) Date: Oct. 25, 2012

(87) PCT Pub. No.: WO2011/113729
PCT Pub. Date: Sep. 22, 2011

(65) Prior Publication Data
US 2013/0204047 A1 Aug. 8, 2013

(30) Foreign Application Priority Data

Mar. 13, 2010 (EP) .................................... 10002671

(51) Int. Cl.
*C07C 41/02* (2006.01)
*C08G 18/28* (2006.01)
*C08G 18/48* (2006.01)
*C08G 65/26* (2006.01)

(52) U.S. Cl.
CPC ............. *C07C 41/02* (2013.01); *C08G 18/283* (2013.01); *C08G 18/4883* (2013.01); *C08G 65/2609* (2013.01); *C08G 65/2696* (2013.01); *C08G 2650/26* (2013.01)

(58) Field of Classification Search
USPC ......................................................... 568/679
See application file for complete search history.

(56) References Cited

U.S. PATENT DOCUMENTS

| | | |
|---|---|---|
| 2,902,478 A | 9/1959 | Anderson |
| 3,085,085 A | 4/1963 | Wismer et al. |
| 3,153,002 A | 10/1964 | Wismer et al. |
| 3,190,927 A | 6/1965 | Patton, Jr. et al. |
| 3,941,769 A | 3/1976 | Maassen et al. |
| 4,332,936 A | 6/1982 | Nodelman |
| 4,385,173 A | 5/1983 | Dix et al. |
| 4,409,187 A | 10/1983 | Köhler et al. |
| 4,430,490 A | 2/1984 | Doerge |
| 2010/0261870 A1 * | 10/2010 | Loeffler et al. ............... 528/425 |

FOREIGN PATENT DOCUMENTS

| | | |
|---|---|---|
| DE | 147469 A3 | 4/1981 |
| DE | 216248 A1 | 12/1984 |
| DE | 219204 A1 | 2/1985 |
| DE | 146606 A1 | 2/1987 |
| DE | 4209358 A1 | 9/1993 |
| DE | 10237914 A1 | 2/2004 |
| DE | 10237918 A1 | 2/2004 |
| FR | 1285708 A | 2/1962 |

* cited by examiner

*Primary Examiner* — Rosalynd Keys
(74) *Attorney, Agent, or Firm* — N. Denise Brown; Lyndanne M. Whalen

(57) ABSTRACT

The present invention relates to is coupling process for the preparation of polyether polyols starting from highly functional starter compounds that are solid or highly viscous under reaction conditions and monofunctional starter compounds that are liquid under reaction conditions with Zerewitinoff-active hydrogen atoms.

13 Claims, 2 Drawing Sheets

GPC spectrum of the residue (polyether polyol A-1, 98 wt.%)

GPC spectrum of the distillate (monofunctional polyether polyol B-1)

METHOD FOR PRODUCING POLYETHER POLYOLS

The present invention relates to a coupling process for the preparation of polyether polyols starting from highly functional starter compounds that are solid or highly viscous under reaction conditions and monofunctional starter compounds that are liquid under reaction conditions with Zerewitinoff-active hydrogen atoms. A highly functional compound within the scope of the invention denotes a compound that has at least four Zerewitinoff-active hydrogen items (i.e. that has, for example, hydroxy and/or amine functionality).

Polyols based on highly functional starter compounds such as, for example, sugars, oligo- and poly-saccharides, sugar alcohols (such as, for example, mannitol or sorbitol) as well as pentaerythritol are generally used in polyurethane applications, in particular in the production of rigid polyurethane foams, which are used for the insulation of refrigeration devices, refrigerated containers or also in the insulation of buildings. Polyol formulations based on such polyols prepared on the basis of highly functional starter compounds can be processed with polyisocyanates to give rigid foams, it being possible for insulating elements produced therefrom (such as, for example, refrigerator casings or insulating panels) to be removed quickly from the foaming moulds without the occurrence of appreciable deformation of the insulating elements.

Sugars (sucrose), other oligo- and poly-saccharides and condensation products such as pentaerythritol, dipentaerythritol, tripentaerythritol and trimethylolethane generally have melting points which are close to or above the reaction temperature for the preparation of polyether polyols by alkylene oxide addition or they decompose before the melting temperature is reached. The prior art therefore knows many processes for making such starter compounds amenable to alkylene oxide addition reactions. For example, it is possible to use solvents for suspending the solid starters, as described in U.S. Pat. No. 4,332,936. It is found to be a disadvantage here that valuable reactor volume must be made available for the solvent, and the use of organic solvents is generally undesirable for reasons of sustainability and product hygiene.

The starter compounds that are solid or highly viscous under reaction conditions or that decompose below or at reaction temperature can further be reacted with alkylene oxide in the presence of other starter compounds that are liquid under reaction conditions. Such procedures are described in U.S. Pat. No. 3,153,002, DE-A 2241242, DD-A 146606, DD-A 147469, DD-A 219204, DD-A 216248, DE-A 3011083, DE-A 4209358, DE-A 10237918 and DE-A 10237914. These processes without exception make use of the mixed starting of the starter compounds that are solid or highly viscous under reaction conditions or that decompose below or at reaction temperature with other, liquid starter compounds that have hydroxy or amine functionalities of from 2 to 6 and are suitable for suspending or partially dissolving those starters. There are necessarily obtained end products having lower functionalities than those of the pure high-melting or high viscosity and/or decomposition-sensitive starter compounds. Such mix-started polyols are therefore less suitable for the production of modern rigid foam formulations, which must satisfy the highest requirements in terms of the demouldability of the insulating elements produced therefrom.

Alkylene oxide addition products of polyfunctional starter compounds can also be used as suspending agents, as described, for example, in FR-A 1285708 and U.S. Pat. No. 3,190,927. If the end products themselves or intermediates based on the starter compounds that are solid or highly viscous under reaction conditions or that decompose below or at reaction temperature are used, it is in principle possible to obtain polyether polyols based only on the high-melting or decomposition-sensitive starter compounds. The inadequate dissolving power of the end products for the highly functional starter compounds has been found to be a disadvantage; in addition, as when solvents are used, valuable reactor volume must be sacrificed for the suspending agent.

If water is used as the suspending agent/solvent for the starter compounds that are solid or highly viscous under reaction conditions or that decompose below or at reaction temperature, the alkylene oxide addition reaction can be interrupted at a suitable point and the still unreacted water can be distilled off. Such procedures are described in DE-A 1443022 and U.S. Pat. No. 4,430,490. These so-called water processes have the disadvantage that the water used as suspending agent and solvent also reacts to a certain degree in the alkylene oxide addition reaction, and on the one hand the functionality of the end products accordingly falls and is also less easily controllable than when co-starters containing hydroxy groups or amine groups are used. On the other hand, glycol-containing waste water is formed, which must either be purified or the glycol content of which must be adjusted to a constant value on recycling into the process.

A process by which polyether polyols started purely on the basis of sucrose are obtainable is described in U.S. Pat. No. 2,902,478. Trimethylamine is used as catalyst, and the monomer propylene oxide is used as suspending agent. Such a reaction procedure is full of risk and is therefore not recommended for safety reasons.

U.S. Pat. No. 4,385,173 and DD-A 200427 describe procedures which are expensive in terms of apparatus and with which it is possible to obtain polyether polyols started purely on the basis of starter compounds that are solid or highly viscous under reaction conditions or that decompose below or at reaction temperature. The reactor types that are employed are not universally usable, that is to say are unsuitable for alkylene oxide addition reactions on other starter compounds.

SUMMARY OF THE INVENTION

It was an object of the present invention to find a process for the preparation of polyether polyols that are as highly functional as possible and are based on highly functional starter compounds, wherein the highly functional starter compounds to be used melt close to or just above the conventional reaction temperature of alkylene oxide addition processes of approximately 100° C., or possess too high a viscosity in the region of the reaction temperature of approximately 100° C., which process does not exhibit the described disadvantages of the processes of the prior art. Preferably, the polyether polyol resulting from the highly functional starter compound should be prepared in such a form that not more than 15 wt. % of a polyether polyol resulting from a further starter compound is present.

Surprisingly, it has been found that the object is achieved by a coupling process for the preparation of a first polyether polyol A and of a second, monofunctional polyether polyol B, characterised in that
  (i) a solution or dispersion of one or more starter compounds (S-1), each having at least four Zerewitinoff-active hydrogen atoms, in one or more monofunctional starter compounds (S-2) is prepared, the weight ratio of S-1 to S-2 being from 20:80 to 85:15, preferably from 50:50 to 85:15, particularly preferably from 60:40 to 85:15, (ii) the solution or dispersion resulting from step (i) is reacted with one or more alkylene oxides, optionally after addition of a catalyst, the reaction product of the at least one starter compound (S-1) with one or more alkylene oxides being the polyether polyol A, and the reaction product of the at least one monofunctional starter compound (S-2) with one or more arkylene oxides being the monofunctional polyether polyol B, (iii) the resulting mixture is optionally freed of catalyst, and (iv) the monofunctional polyether polyol B is separated off by distillation under reduced pressure or by stripping with inert gas or water, the residue that remains containing poly:ether polyol A and up to 15 wt. % (in each case based on the sum of the wt. % of polyether polyol A and of the monofunctional polyether polyol B) monofunctional polyether polyol B.

DETAILED DESCRIPTION OF THE INVENTION

Figure 1:
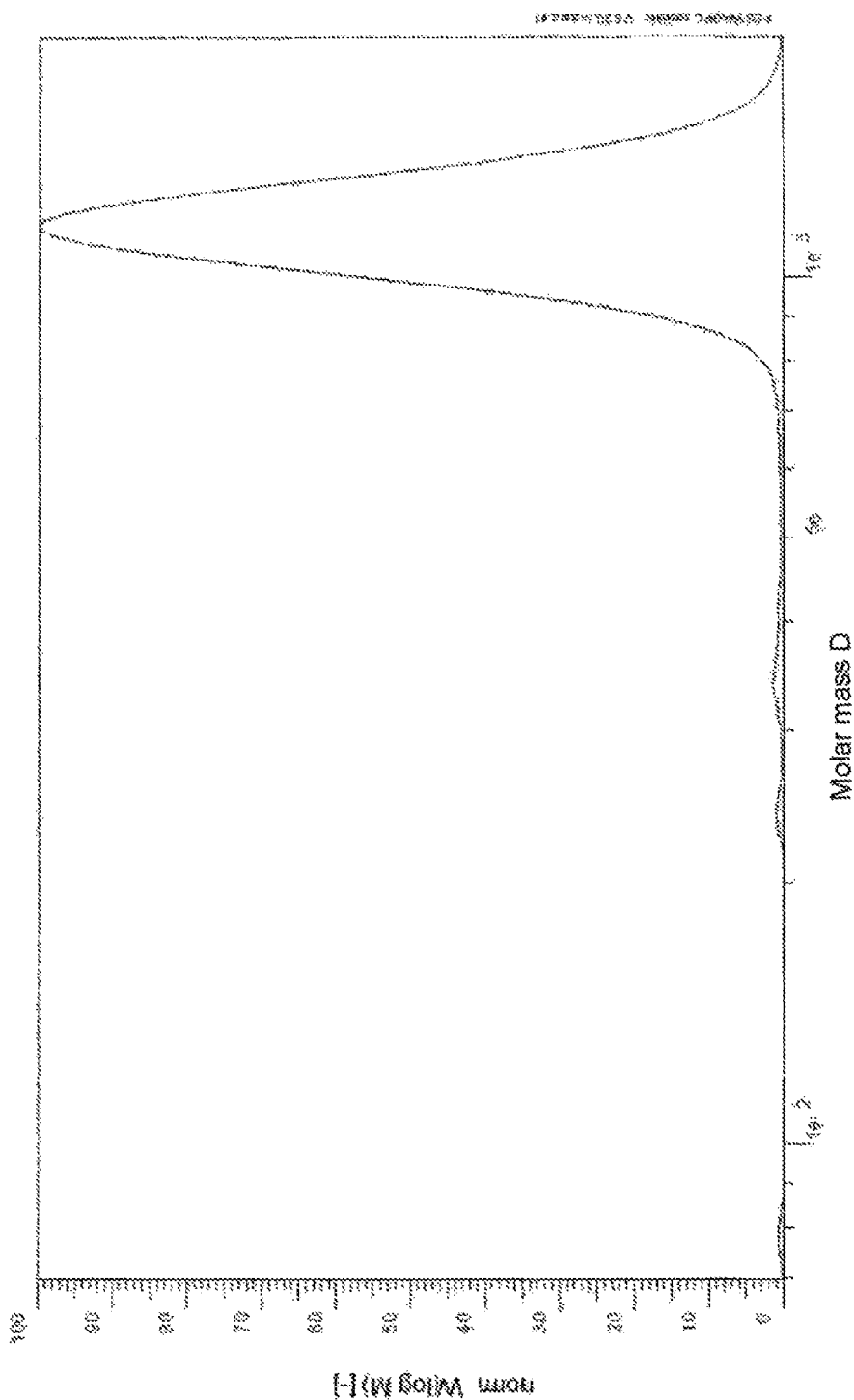
FIG. 1 is a gas phase chromatograph (GPC) spectrum of the residue generated in Example 1.

The process according to the invention has the advantage that highly functional starter compounds (S-1) that are still solid or too viscous at reaction temperature can be used for the alkoxylation. The monofunctional polyethers formed from the alkoxylation of the monofunctional starter compounds (S-2) which are likewise used in the process can be removed from the reaction mixture by distillation, so that the highly functional alkylene oxide addition products resulting from the at least one starter compound (S-1) can be isolated in high purity (i.e. at least 85 wt. %). The highly functional alkylene oxide addition products can be processed as components of rigid foam formulations with polyisocyanates, the resulting insulating elements satisfying the highest requirements in terms of demouldability. The highly functional alkylene oxide addition products can likewise be subjected to further alkylene oxide addition reactions, whereby highly functional polyether polyols with high equivalent molar masses which are not readily obtainable by other means become accessible. The monofunctional polyethers removed by distillation are in turn used, for example, as valuable solvents or as starter compounds for higher molecular weight monofunctional polyethers, which can be used, for example, as surfactants or as lubricants.

Hydrogen bonded to N, O or S is referred to as Zerewitinoff-active hydrogen (or as "active hydrogen") when it yields methane by reaction with methylmagnesium iodide according to a process discovered by Zerewitinoff. Typical examples of compounds having Zerewitinoff-active hydrogen are compounds containing carboxyl, hydroxyl, amino, imino or thiol groups as functional groups.

The starter compound(s) (S-1) is/are at least one compound selected from the group consisting of mono-, oligo- and polysaccharides, pentaerythritol, dipentaerythritol, tripentaerythritol, sorbitol, cyclic polyols (such as, for example, inositol), polyamines (such as, for example, compounds based on highly functional polynuclear aniline/formaldehyde condensation products ("polymeric MDA")) and isomers or isomer mixtures of toluylenediamine (in particular 2,4-TDA, 2,6-TDA, 2,3-TDA, 3,4-TDA). Sucrose and/or pentaerythritol is/are preferably used as the starter compound (S-1), and sucrose is particularly preferably used. The starter compounds (S-1) are generally in solid form at 70° C. (this is usually the lower limit of the reaction temperature range in alkoxylations) or they are highly viscous (i.e. they have a viscosity of 100 mPas or more at 70° C.).

The monofunctional starter compound(s) (S-2) is/are at least one compound selected from monofunctional alcohols, short-chained monoalkyl ethers of glycols (for example ethylene glycol monomethyl ether or diethylene glycol monomethyl ether), higher monofunctional fatty alcohols (for example monofunctional fatty alcohols having from 8 to 30 carbon atoms such as, for example, 10-undecen-1-ol or 1-decanol), monofunctional amines (for example dimethylamine, methylethylamine, diethylamine) and monofunctional alkanolamines (such as, for example, 2-(dimethylamino)-ethanol and 1-(dimethylamino)-2-propanol). The monofunctional starter compound(s) (S-2) is/are preferably at least one compound selected from methanol, ethanol, propanol (for example 1-propanol, isopropartol), butanol (for example 1-butanol, 2-butanol), pentanol (for example 1-pentanol, 2-pentanol) and hexanol (for example 1-hexanol, 2-hexanol, 2-methyl-1-pentanol); the monofunctional starter compound (S-2) is particularly preferably methanol. The starter compounds (S-2) are preferably in liquid form at 100° C., particularly preferably even at 70° C.

The at least one starter compound (S-1) is dispersed or dissolved in the at least one monofunctional starter compound (S-2) ("co-starter"). The ratio between starter compounds (S-1) and monofunctional starter compounds (S-2) can be varied within wide limits. The ratio chosen in a particular case depends on the one hand on the desired product mix; on the other hand, sufficient stirrability of the dispersion or solution of the starter compounds (S-1) in the monofunctional starter compounds (S-2) must naturally be ensured. For example, ratios of 75 wt. % sucrose and 25 wt. % methanol have been found to be very suitable for the process according to the invention.

In a preferred embodiment of the process according to the invention, a catalyst is added to the dispersion or solution of the at least one starter compound (S-1) in the at least one monofunctional starter compound (S-2). For example, double metal cyanide compounds (DMC compounds) can be added as catalysts. DMC catalysts, as described, for example, in U.S. Pat. No. 5,470,813, U.S. Pat. No. 6,696,383, EP-A 0 700 949, EP-A 0 743 093, EP-A 0 761 708, WO-A 97/40086, WO-A 98/16310 and WO-A 00/47649, have high activity in alkylene oxide addition reactions on starter compounds with Zerewitinoff-active hydrogen atoms and permit the preparation of polyether polyols at very low catalyst concentrations (50 ppm or less), so that it is no longer necessary to separate the DMC catalyst from the polyether polyol before the processing thereof to polyurethanes, for example polyurethane foams. The economy of the industrial polyether polyol production is increased markedly as a result. Alternatively, the process according to the invention can also be catalysed by Lewis acids such as, for example, boron trifluoride etherate. However, such catalysts are of lesser importance owing to their tendency to form secondary products.

In the process according to the invention there are preferably used basic catalysts such as, for example, alkali metal hydrides, alkali metal carboxylates (for example of monofunctional carboxylic acids), alkali metal hydroxides, alkali metal alkoxides (for example of monofunctional alcohols) or amines. An overview of amines suitable for the process according to the invention has been given by M. Ionescu et al. in "Advances in Urethanes Science and Technology", 1998, 14, p. 151-218. There can be used, for example, N,N-dimethylbenzylamine, dimethylaminopropanol, N-methyldiethanolamine, trimethylamine, triethylamine, N,N-dimethylcyclohexylamine, N-methylpyrrolidine, N,N,N',N'-tetramethylethylenediamine, diazabicyclo[2.2.2]octane, 1,4-dimethylpiperazine, N-methylmorpholine, unsubstituted imidazole and/or alkyl-substituted imidazole derivatives. There are particularly preferably used in the process according to the invention as basic catalysts alkali metal hydroxides (such as, for example, sodium hydroxide, potassium hydroxide or caesium hydroxide), alkali metal alkoxides of monofunctional alcohols (such as, for example, potassium alcoholates of monofunctional alcohols, particularly preferably potassium methanolate), imidazole or alkyl-substituted imidazole derivatives (such as, for example, N-methylimidazole). The alkali metal hydroxides can be used in solid form or in the form of highly concentrated aqueous solutions.

The basic catalysts are preferably used in amounts of from 0.004 to 0.8 wt. %, preferably from 0.004 to 0.15 wt. %, based on the end product amount (i.e. the sum of the resulting polyether polyols A and B). When catalysts based on alkali metal hydroxides are used or when N-methyldiethanolamine is used, it is to be noted that small amounts of dihydroxyfunctional polyether molecules can form during the alkylene oxide addition reaction, but these do not significantly affect the functionality of the end product at the catalyst amounts that are conventionally employed. If at least one monofunctional amine is used as monofunctional starter compounds (S-2) and/or at least one polyamine or isomers or isomer mixtures of toluyienediamine are used as starter compounds (S-1), no catalyst is added in step (ii) in a preferred embodiment of the invention.

To the solution or dispersion containing at least one starter compound (S-1) and at least one monofunctional starter compound (S-2) resulting from step (i) there is added continuously at least one alkylene oxide, preferably under an inert gas atmosphere (step (ii), "Alkoxylation"). The alkylene oxide is preferably at least one selected from the group consisting of ethylene oxide, propylene oxide, 1,2-butylene oxide, 2,3-butylene oxide and styrene oxide. Particular preference is given to ethylene oxide, propylene oxide or a mixture of propylene oxide and ethylene oxide. The alkylene oxides can be fed to the reaction mixture individually, in a mixture or in succession. If the alkylene oxides are metered in succession, the polyether polyols that are prepared contain polyether chains having block structures. Products having ethylene oxide blocks are characterised, for example, by an increased content of primary end groups, which give the polyether polyol increased reactivity towards isocyanates. The choice of the alkylene oxide used in a particular case and the arrangement thereof within the polyether chains is made in view of the desired properties of the polyether polyols A and B that are to be obtained.

The alkoxylation takes place preferably at a temperature of from 70 to 170° C., particularly preferably at a temperature of from 100 to 130° C. The temperature can be varied during the alkylene oxide metering phase (step (ii)) within the described limits: In order to achieve an optimum balance between high alkylene oxide conversion and low secondary product formation when using sensitive starter compounds (such as, for example, sucrose), it is possible initially to carry out the alkoxylation at low reaction temperatures (for example at from 70 to 110° C.) and to change to higher reaction temperatures (for example from 110 to 130° C.) only when sufficient conversion of the starters has been achieved (i.e. as soon as at least 50 wt. % of the starter compounds used have reacted on at least one Zerewitinoff-active hydrogen atom with alkylene oxide). Post-reactions can likewise be carried out at higher temperatures (i.e. after the temperature has been increased to 100 to 170° C., preferably 100 to 150° C.). The temperature of the exothermic alkylene oxide addition reaction is maintained at the desired level by cooling. According to the prior art relating to the design of polymerisation reactors for exothermic reactions (e.g. Ullmann's Encyclopedia of Industrial Chemistry, Volume B4, page 167ff, 5th Edition, 1992), such cooling is generally carried out via the reactor wall (e.g. double-wall, half-pipe coil) as well as by means of further heat-exchange surfaces arranged internally in the reactor and/or externally in the recirculation loop, for example at cooling coils, cooling rods, plate heat exchangers, tubular heat exchangers or mixer-heat exchangers. These are advantageously to be so designed that effective cooling can be carried out even at the beginning of the metering phase, that is to say with a low fill level, and in the presence of a heterogeneous reactor content (for example where solids dispersions are present).

In general, thorough mixing of the reactor contents is to be ensured in all reaction phases by the design and use of conventional stirring members, there being suitable in particular stirrers arranged in one or two stages or stirrer types which are active over a large area of the filling height (see, for example, Handbuch Apparate; Vulkan-Verlag Essen, 1st edition (1990), p. 188-208). Of particular technical relevance here is an average volume-specific mixing power introduced over the entire reactor contents of generally in the range from 0.2 to 5 with correspondingly higher volume-specific local power inputs in the region of the stirring members themselves and optionally at lower filling levels. In order to achieve an optimum stirring action, it is possible according to the general prior art to arrange in the reactor a combination of baffles (e.g. flat or tubular baffles) and cooling coils (or cooling plugs), which can also extend over the bottom of the container. The stirring power of the mixing unit can also be varied during the metering phase in dependence on the filling level, in order to ensure a particularly high energy input in critical reaction phases. For example, it can be advantageous to mix solids-containing dispersions, which may be present at the beginning of the reaction when sucrose is used, particularly intensively. In addition, when using solid starters it is to be ensured, by the choice of stirring unit, that the solid is dispersed sufficiently in the reaction mixture. Stirring stages acting close to the bottom as well as stirring members suitable in particular for suspension are preferably used here.

Furthermore, the stirrer geometry should contribute towards reducing the foaming of reaction products, such as, for example, after the end of the metering and post-reaction phase when separating residual epoxides in vacuo. Stirring members that achieve continuous thorough mixing of the liquid surface have been found to be suitable here. Depending on the requirement, the stirrer shaft has a bottom bearing and optionally further support bearings in the container. Driving of the stirrer shaft can take place from the top or bottom (with centred or eccentric arrangement of the shaft). Alternatively, it is of course also possible to achieve the necessary thorough mixing solely by means of a recirculation loop guided via a heat exchanger or to operate the recirculation loop as a further mixing component in addition to the stirring unit, the reactor contents being recirculated as required (typically from 1 to 50 times per hour).

The continuous metered addition of the at least one alkylene oxide is carried out in such a manner that the safety-related pressure limits are not exceeded. These are governed, of course, by the apparatus-related conditions that are present in an individual case, the process generally being carried out in a pressure range from 1 mbar to 10 bar, particularly preferably from 1 mbar to 4 bar. In the metered addition in particular of alkylene oxide mixtures containing ethylene oxide or of pure ethylene oxide, it is advantageously to be ensured that an adequate inert gas partial pressure is maintained in the reactor during the start-up and metering phase. This can be established, for example, by noble gases or nitrogen.

The at least one alkylene oxide can be fed to the reactor in different ways: Metering into the gas phase or directly into the liquid phase is possible, for example via a submerged pipe or a distributor ring located in the vicinity of the reactor bottom in a zone with thorough mixing. If an alkylene oxide mixture is metered in, the alkylene oxides can be fed to the reactor separately or as a mixture. Pre-mixing of the alkylene oxides can be achieved, for example, by a mixing unit located in the common metering line ("inline blending"). It has also proved successful to meter alkylene oxides individually or as a premixture into the recirculation loop on the pump pressure side. For thorough mixing with the reaction medium, it is then advantageous to integrate a high-shear mixing unit into the alkylene oxide/reaction medium stream. At the end of the alkylene oxide metering there preferably follows a post-reaction, the end of which is reached as soon as no further pressure drop is observed in the reaction vessel. Residual contents of alkylene oxide can then optionally be removed by a vacuum, inert gas or steam stripping step. It is also possible for residual contents of alkylene oxide not to be removed until step iv) is carried out, that is to say the separation of the monofunctional polyether polyol B by distillation. The OH number of the crude mixture (containing polyether polyol A and monofunctional polyether polyol B) resulting from step ii) is generally from 150 to 1200 mg KOH/g, preferably from 200 to 1200 mg KOH/g and particularly preferably from 270 to 1200 mg KOH/g.

A very wide variety of reactor types are generally suitable for carrying out the process according to the invention. Cylindrical containers having a height to diameter ratio of from 1:1 to 10:1 are generally used. Suitable reactor bottoms are, for example, spherical, dished, flat or cone-shaped bottoms.

The crude mixture resulting from step ii) can optionally be subjected to working-up steps in order to remove any traces of catalyst (step iii)). In the case of alkylene oxide addition reactions catalysed with amines or with highly active DMC compounds, such after-treatment steps are generally not required. The optional removal of the catalyst from the crude mixture resulting from step ii) can be carried out in various ways: For example, the basic catalyst can be neutralised with dilute mineral acids such as sulfuric acid or phosphoric acid. The salts formed in the neutralisation are separated off, for example by filtration. Exceptions are the polyether polyol preparation processes described in EP-A 2028211 and WO-A 2009106244. Alternatively, the neutralisation can be carried out with hydroxycarboxylic acids (such as, for example, lactic acid, as described in WO-A 9820061 and US-A 2004167316). Likewise suitable for the neutralisation are carboxylic acids such as, for example, formic acid (see U.S. Pat. No. 4,521,548). The metal carboxylates formed after neutralisation with carboxylic acids (such as, for example, hydroxycarboxylic acids or formic acid) dissolve in the polyether polyols to form a clear solution, so that separation of the salts is not required here. It is likewise possible to remove the catalyst using acid cation exchangers, as described, for example, in DE-A 100 24 313. Furthermore, the catalysts can be separated off by means of adsorbents such as, for example, sheet silicates (bentonite, attapulgite), diatomaceous earth or also synthetic magnesium silicates (such as AMBOSOL® or BriteSorb®). Such purification processes are described in RO 118433, U.S. Pat. No. 4,507,475, EP-A 0693513 and EP-A 1751213. Phase separation processes are in principle likewise possible, but the water solubilities of the highly functional and monofunctional constituents of the reaction mixture are generally too high for phase separation processes to be carried out effectively. Phase separation processes are described, for example, in WO-A 0114456, JP-A 6-157743, WO-A 9620972 and U.S. Pat. No. 3,823,145.

In step iv) of the process according to the invention, the monofunctional polyether polyol B is removed from the polyether polyol mixture obtained after alkoxylation (step ii)) and optionally after removal of the catalyst (step iii)) by means of distillation under reduced pressure or by means of stripping with inert gas or water, the distillation residue that remains containing the polyether polyol A and up to 15 wt. % monofunctional polyether polyol B. Separation of the monofunctional polyether polyol B can also be effected with the aid of thin-layer evaporators, falling film evaporators or spiral tube evaporators, it being possible here too for the separation process to be assisted by the introduction of inert gas streams. Such processes and apparatuses are described, for example, in "Perry's Chemical Engineers' Handbook"; 6th international edition; 1984; editors: R. H. Perry, D. W. Green, J. O. Maloney; McGraw-Hill Book Company on p. 11-34 or in Chapter 18, additionally in DE 2755089 and WO-A 2010003734. The distillation or stripping temperatures can be chosen within a wide range. They are governed by the thermal stability of the crude polyether mixture; in particular, they are determined by the thermal stability of the polyether polyol A. In general, they are from 100 to 200° C. If short-path evaporator apparatuses are used, higher temperatures can also be chosen because shorter residence times of the products on the heated surfaces can generally be achieved here.

Alternatively, it is also possible first to carry out the separation according to step iv) and then to remove the catalyst from the monofunctional polyether polyol B or the residue containing polyether polyol A and up to 15 wt. % monofunctional polyether polyol B.

The residue that remains according to step iv) contains preferably from 85 to 100 wt. %, particularly preferably from 95 to 100 wt. %, polyether polyol A and preferably from 0 to 15 wt. %, particularly preferably from 0 to 5 wt. % (in each case based on the sum of the wt. % of polyether polyol A and of the monofunctional polyether polyol B) monofunctional polyether polyol B.

The separate constituents of polyether polyol A and monofunctional polyether polyol B obtainable by the process according to the invention can each be subjected to further alkylene oxide addition reactions, that is to say can be reacted with one or more of the above-mentioned alkylene oxides. In general, the catalysts mentioned above are suitable for this purpose. The same catalyst as in step ii) or a catalyst other than the catalyst used in step ii) can be employed in the further alkylene oxide addition reactions. The addition of catalyst is generally carried out when the catalyst has already been separated off according to step iii) before the separation of the polyether polyol mixture (step iv)). The addition of catalyst to polyol B preferably also takes place if a low-volatility catalyst was used in step ii) which is not available for a further alkylene oxide addition on polyol B. A change of catalyst is possible in the further alkylene oxide addition reactions, for example from basic catalyst types to acid catalyst types or to DMC catalysts. If the process according to the invention is carried out without separating off the catalyst according to step iii), the catalyst amounts remaining in polyether polyol A and the monofunctional polyether polyol B can also serve directly as catalyst in the further alkylene oxide addition reaction. The catalyst amounts that remain in polyether polyol A and/or polyol B are optionally to be supplemented before further alkylene oxide addition reactions are carried out. A preferred embodiment of the invention is accordingly a coupling process for the preparation of a second polyether polyol C and a second, monofunctional polyether polyol D, characterised in that (i) a solution or dispersion of one or more starter compounds (S-1), each having at least four Zerewitinoff-active hydrogen atoms, in one or more monofunctional starter compounds (S-2) is prepared, the weight ratio of S-1 to S-2 being from 20:80 to 85:15, preferably from 50:50 to 85:15, particularly preferably from 60:40 to 85:15, (ii) the solution or dispersion resulting from step (i) is reacted with one or more alkylene oxides with the addition of a catalyst selected from the group consisting of the basic catalysts, the reaction product of the at least one starter compound (S-1) with one or more alkylene oxides being the polyether polyol and the reaction product of the at least one monofunctional starter compound (S-2) with one or more alkylene oxides being the monofunctional polyether polyol B, (iii) the resulting mixture is not freed of catalyst, (iv) the monofunctional polyether polyol B is separated off by distillation under reduced pressure or by stripping with inert gas or water, the residue that remains containing polyether polyol A and up to 15 wt. % (in each case based on the sum of the wt. % of the polyether polyol A and of the monofunctional polyether polyol B) monofunctional polyether polyol B, and (v) (1) the residue that remains containing polyether polyol A and up to 15 wt. % (in each case based on the sum of the wt. % of the polyether polyol A and of the monofunctional polyether polyol 3) monofunctional polyether polyol B, optionally after addition of further catalyst, is reacted with one or more alkylene oxides, polyether polyol C being obtained, and/or (2) the monofunctional polyether polyol B, optionally after addition of further catalyst, is reacted with one or more alkylene oxides, polyether polyol D being obtained.

Antioxidants (e.g. based on phenol derivatives and/or based on amines) can be added to the polyether polyol A and/or the monofunctional polyether polyol B as well as to the polyether polyol C and to the polyether polyol D. Such antioxidants are generally added only after basic, in particular alkali-metal-containing, catalyst traces have been separated off, because discolouration of the polyether polyol in question can thus be avoided.

The polyether polyols A, B, C and/or D obtainable by the process according to the invention can be used as starting components for the production of solid or foamed polyurethane materials as well as of polyurethane elastomers. The polyurethane materials and elastomers can also contain isocyanurate, allophanute and biuret structural units, it is also possible to produce so-called isocyanate prepolymers, the production of which involves the use of at least one (poly)isocyanate and at least one polyether polyol A, B, C and/or D, wherein the molar ratio of isocyanate groups to hydroxy groups is greater than 1, so that the resulting prepolymers contain isocyanate groups. These isocyanate groups of the prepolymers can be reacted in one or more steps with compounds containing Zerewitinoff-active hydrogen atoms in order to produce the actual end product, such as solid or foamed polyurethane materials as well as polyurethane elastomers.

For the production of solid or foamed polyurethane materials as veil as of polyurethane elastomers, the polyether polyols A, B, C and/or D according to the invention are optionally mixed with further isocyanate-reactive components and reacted with organic polyisocyanates, optionally in the presence of blowing agents in the presence of catalysts, optionally in the presence of other additives such as, for example, cell stabilisers.

EXAMPLES

Ambosol®:
Precipitated, colloidal, synthetically produced magnesium silicate (composition: 2.7 $SiO_2$, MgO, 1.5 $H_2O$)
Catalyst:
25 wt. % solution of potassium methoxide (potassium methanolate) in methanol
Methods:
The OH numbers were determined as specified in DIN 53240.
The molar mass distribution was determined by means of size exclusion chromatography (SEC). An Agilent 100 Series device from Agilent was used. The polydispersity (PD) for the molecular weight distribution $M_w/M_n$ is given, where $M_w$ represents the weight-average molar mass and $M_n$ represents the number-average molar mass. Further details:
Column combination: 1 PSS precolumn, 5 µl, 8×50 mm; 2 PSS SVD, 5 µl, 100 A°, 8×300 mm; 2 PSS SVD, 5 µl, 1000 A°, 8×300 mm, PSS is the manufacturer of the columns (Polymer Standard Solutions, Mainz)
Evaluation software: WIN GPC from PSS
Solvent: THE (Merck LiChrosolv)
Flow rate: 1 ml/min
Detector type: RI detector (refractive index), Shodex RI 74
Calibration standard used: PSS calibration standard based on polystyrene.

Example 1

52.46 g of methanol, 140.9 g of sucrose and 10.3 g of a 25% solution of potassium methoxide in methanol were placed in a 2-liter laboratory autoclave under a nitrogen atmosphere. Residual oxygen was removed after closure of the filling nozzle by filling the apparatus three times with 3.0 bar nitrogen each time and then letting off the excess pressure to atmospheric pressure. The contents of the autoclave were heated to 110° C., with stirring (800 rpm). 486 g of propylene oxide were metered into the autoclave at a stirrer speed of 800 rpm over a period of 3.0 hours. The metered addition of propylene oxide was started at a pressure of 5.0 bar and the maximum pressure reached during the metering phase was 6.0 bar. When the metered addition of propylene oxide was complete, there followed a post-reaction time of 8 hours. After a heating phase of 30 minutes in vacuo (10 mbar), the resulting mixture was cooled to 80° C., with stirring, and 20 g of Ambosol® were added as adsorbent. Stirring was carried out for 2 hours, followed by filtering over a depth filter (T 750) in order to separate off the adsorbent.

Figure 2:
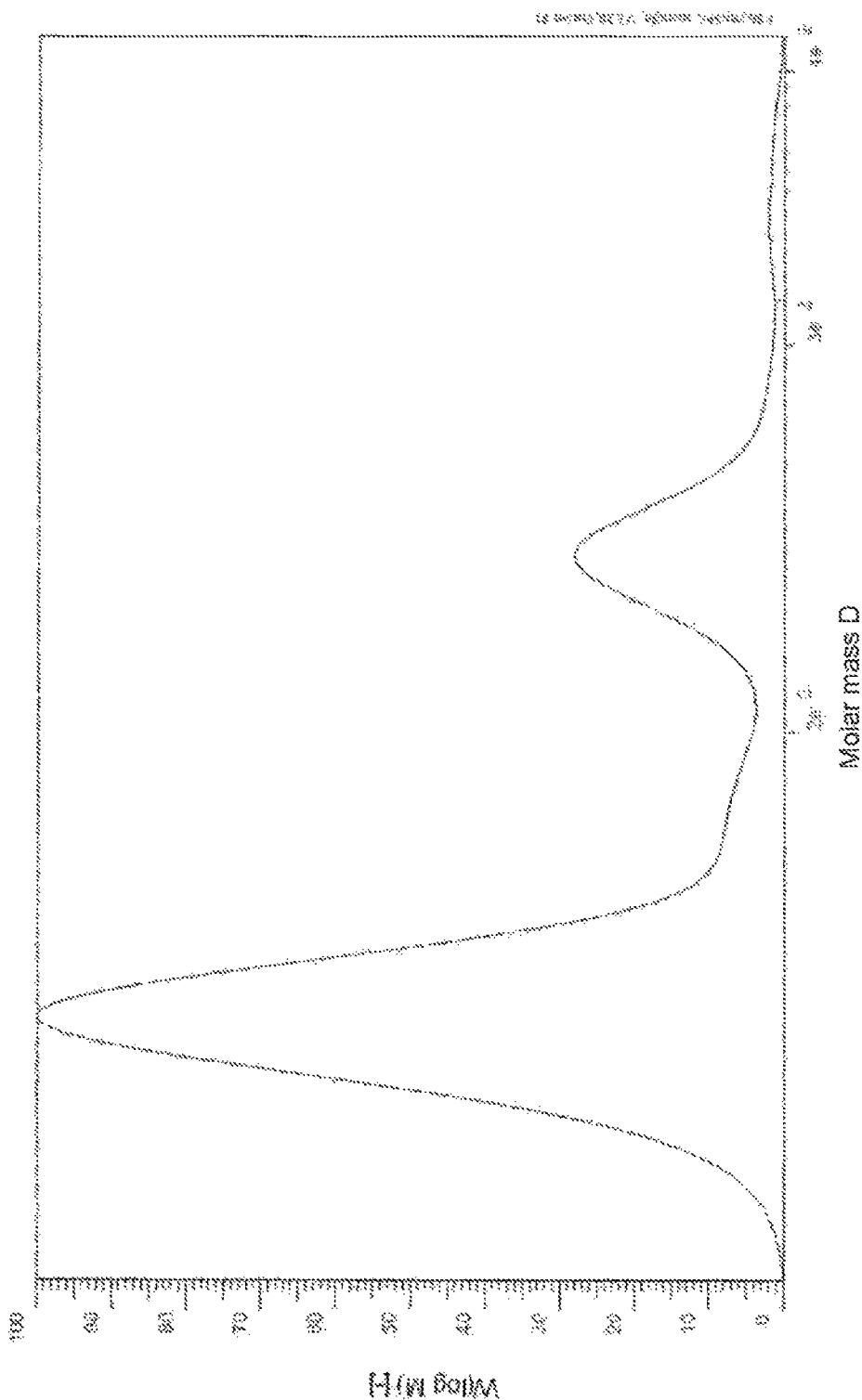
FIG. 2 is a GPC spectrum of the distillate from Example 1.

251.6 g of the resulting filtrate were first stirred for 9.5 hours at 120° C. and 1 mbar, 42.87 g of distillate (monofunctional polyether polyol B-1, based on methanol as starter compound) being separated off by means of distillation. Stripping with nitrogen was then carried out for a further 10 hours at 150° C., that is to say, under an applied vacuum (produced by means of an oil pump), a slight stream of nitrogen was passed into the liquid phase, with stirring, by means of a glass tube. It was thereby possible to collect a further 2.6 g of volatile material (monofunctional polyether polyol B-1) in the receiver and the cooling trap. The two distillate fractions were combined and analysed by means of GPC (FIG. 2, monofunctional polyether polyol B-1). The residue showed a polydispersity (PD) of 1.09, its OH number was 370 mg KOH/g. From the integrals of the signals of the GPC spectrum of the residue (FIG. 1), the proportion of polyether polyol A-1 (based on sucrose as starter compound) in this residue was calculated at 98 wt. %. The evaluation of the GPC spectrum was made on the basis that the signal intensity is proportional to the mass of the species in question. Furthermore, signals below 500 Da were assigned to the monofunctional polyether polyol B-1 and signals above 500 Da were assigned to the polyether polyol A-1.

The invention claimed is:

1. A process for the preparation of a first polyether polyol A and of a second, monofunctional polyether polyol B comprising:
   (i) preparing a solution or dispersion of one or more starter compounds (S-1), each having at least four Zerewitinoff-active hydrogen atoms, in one or more monofunctional starter compounds (S-2) at a weight ratio of S-1 to S-2 of from 20:80 to 85:15,
   (ii) reacting the solution or dispersion from step (i) with one or more alkylene oxides, optionally after addition of a catalyst, to form a reaction mixture that includes polyether polyol A that is a reaction product of the at least one starter compound (S-1) with one or more alkylene oxides and polyether polyol B that is a reaction product of the at least one monofunctional starter compound (S-2) with one or more alkylene oxides,
   (iii) optionally, removing any catalyst present from the reaction mixture formed in (ii), and
   (iv) separating the monofunctional polyether polyol B from the reaction mixture by distillation under reduced pressure or by stripping with inert gas or water to generate a residue containing polyether polyol A and up to 15 wt. % (in each case based on the sum of the wt. % of polyether polyol A and of the monofunctional polyether polyol B) monofunctional polyether polyol B.

2. The process of claim 1 in which the weight ratio of S-1 to S-2 is from 60:40 to 85:15.

3. The process of claim 1 in which the starter compound (S-1) is at least one compound selected from the group consisting of mono-, oligo- and poly-saccharides, pentaerythritol, dipentaerythritol, tripentaerythritol, sorbitol, cyclic polyols, polyamines, and isomers and isomer mixtures of toluenediamine.

4. The process of claim 3 in which the monofunctional starter compound (S-2) is at least one compound selected from the group consisting of monofunctional alcohols, short-chained monofunctional monoalkyl ethers of glycols, higher monofunctional fatty alcohols, monofunctional amines and monofunctional alkanolamines.

5. The process of claim 1 in which the starter compound (S-1) is sucrose and/or pentaerythritol and the monofunctional starter compound (S-2) is at least one compound selected from the group consisting of methanol, ethanol, propanol, butanol, pentanol and hexanol.

6. The process of claim 1 in which a catalyst selected from the group consisting of double metal cyanide compounds (DMC compounds), alkali metal hydrides, alkali metal carboxylates, alkali metal hydroxides, alkali metal alkoxides and amines is used in step (ii).

7. The process of claim 4 in which a catalyst selected from the group consisting of double metal cyanide compounds (DMC compounds), alkali metal hydrides, alkali metal carboxylates, alkali metal hydroxides, alkali metal alkoxides and amines is used in step (ii).

8. The process of claim 1 in which a catalyst selected from the group consisting of alkali metal hydroxides, alkali metal alkoxides of a monofunctional alcohol, imidazole and alkyl-substituted imidazole derivatives is used.

9. The process of claim 1 in which potassium methanolate is the catalyst used in step (ii).

10. The process of claim 1 in which the residue contains from 95 to 100 wt. % polyether polyol A and from 0 to 5 wt. % (in each case based on the sum of the wt. % of the polyether polyol A and of the monofunctional polyether polyol B) monofunctional polyether polyol B.

11. The process of claim 1 in which
   (i) the weight ratio of S-1 to S-2 is from 20:80 to 85:15,
   (ii) the solution or dispersion resulting from step (i) is reacted with the one or more alkylene oxides in the presence of a basic catalyst,
   (iii) the reaction mixture from (ii) is not freed of catalyst,
   (iv) the monofunctional polyether polyol B is separated from the reaction mixture by distillation under reduced pressure or by stripping with inert gas or water and the residue remaining contains polyether polyol A and up to 15 wt. % (in each case based on the sum of the wt. % of the polyether polyol A and of the monofunctional polyether polyol B) monofunctional polyether polyol B, and
   (v) the residue containing polyether polyol A and up to 15 wt. % (in each case based on the sum of the wt. % of the polyether polyol A and of the monofunctional polyether polyol B) monofunctional polyether polyol B, optionally after addition of a catalyst, is reacted with one or more alkylene oxides, to form polyether polyol C.

12. The process of claim 11 in which (vi) the monofunctional polyether polyol B, optionally after addition of further catalyst, is reacted with one or more alkylene oxides to form polyether polyol D.

13. The process of claim 1 in which
   (i) the weight ratio of S-1 to S-2 is from 20:80 to 85:15,
   (ii) the solution or dispersion resulting from step (i) is reacted with the one or more alkylene oxides in the presence of a basic catalyst,
   (iii) the reaction mixture from (ii) is not freed of catalyst,
   (iv) the monofunctional polyether polyol B is separated from the reaction mixture by distillation under reduced pressure or by stripping with inert gas or water and the residue remaining contains polyether polyol A and up to 15 wt. % (in each case based on the sum of the wt. % of the polyether polyol A and of the monofunctional polyether polyol B) monofunctional polyether polyol B, and
   (vi) the monofunctional polyether polyol B, optionally after addition of further catalyst, is reacted with one or more alkylene oxides to form polyether polyol D.

* * * * *